US008731885B2

(12) United States Patent
Iannotti et al.

(10) Patent No.: US 8,731,885 B2
(45) Date of Patent: *May 20, 2014

(54) METHOD AND APPARATUS FOR PREPARING FOR A SURGICAL PROCEDURE

(71) Applicants: Joseph P. Iannotti, Strongsville, OH (US); Jason Scalise, Phoenix, AZ (US); Jason A. Bryan, Avon Lake, OH (US)

(72) Inventors: Joseph P. Iannotti, Strongsville, OH (US); Jason Scalise, Phoenix, AZ (US); Jason A. Bryan, Avon Lake, OH (US)

(73) Assignee: The Cleveland Clinic Foundation, Cleveland ( * ) Notice: Subject to any disclaimer, the term of this patent is extended or adjusted under 35 U.S.C. 154(b) by 76 days.

This patent is subject to a terminal disclaimer.

(21) Appl. No.: 13/744,658

(22) Filed: Jan. 18, 2013

(65) Prior Publication Data
US 2013/0253893 A1  Sep. 26, 2013

Related U.S. Application Data

(63) Continuation of application No. 13/197,265, filed on Aug. 3, 2011, now Pat. No. 8,380,471, which is a continuation of application No. 12/043,634, filed on Mar. 6, 2008, now Pat. No. 8,014,984.

(60) Provisional application No. 60/905,211, filed on Mar. 6, 2007.

(51) Int. Cl.
*G06G 7/48* (2006.01)

(52) U.S. Cl.
USPC ........................................... 703/6; 623/19.13

(58) Field of Classification Search
USPC ........ 703/6, 11; 700/117; 473/434; 606/86 R, 606/86, 87, 53, 63; 623/16.11, 19, 13, 12, 623/20, 17.11; 601/46; 600/443, 407, 301; 128/898; 382/128

See application file for complete search history.

(56) References Cited

U.S. PATENT DOCUMENTS

| 4,976,737 | A  | * | 12/1990 | Leake           | 128/898   |
|-----------|----|---|---------|-----------------|-----------|
| 5,798,924 | A  | * | 8/1998  | Eufinger et al. | 700/117   |
| 5,871,018 | A  | * | 2/1999  | Delp et al.     | 128/898   |
| 6,932,842 | B1 | * | 8/2005  | Litschko et al. | 623/16.11 |
| 7,542,791 | B2 | * | 6/2009  | Mire et al.     | 600/407   |
| 7,618,419 | B2 | * | 11/2009 | Lavallee        | 606/86 R  |
| 2002/0059049 | A1 | * | 5/2002 | Bradbury et al. | 703/11  |
| 2003/0119611 | A1 | * | 6/2003 | Lytle et al.    | 473/434 |
| 2004/0068187 | A1 | * | 4/2004 | Krause et al.   | 600/443 |
| 2004/0068210 | A1 | * | 4/2004 | Eizenhofer      | 601/46  |
| 2004/0068263 | A1 | * | 4/2004 | Chouinard et al.| 606/86  |
| 2006/0195194 | A1 | * | 8/2006 | Gunther         | 623/19.13 |
| 2007/0173815 | A1 | * | 7/2007 | Murase          | 606/53  |

OTHER PUBLICATIONS

Murphy et al., "The planning of orthopaedic reconstructive surgery using computer aided simulation and design", Computer Medical Imaging, 1988.*

* cited by examiner

*Primary Examiner* — Kandasamy Thangavelu
(74) *Attorney, Agent, or Firm* — Norton Rose Fulbright Canada LLP

(57) ABSTRACT

A method of preparing for a surgical procedure includes creating a three-dimensional bone model of a subject bone of a patient. At least a portion of the bone model is compared to at least one three-dimensional reference anatomic model. At least one structural difference between the bone model and the at least one reference anatomic model is identified. At least one desired subject bone structural change is specified to produce a modified bone model responsive to the step of identifying at least one structural difference between the bone model and the at least one reference anatomic model. An apparatus for preparing for a surgical procedure is also provided.

16 Claims, 7 Drawing Sheets

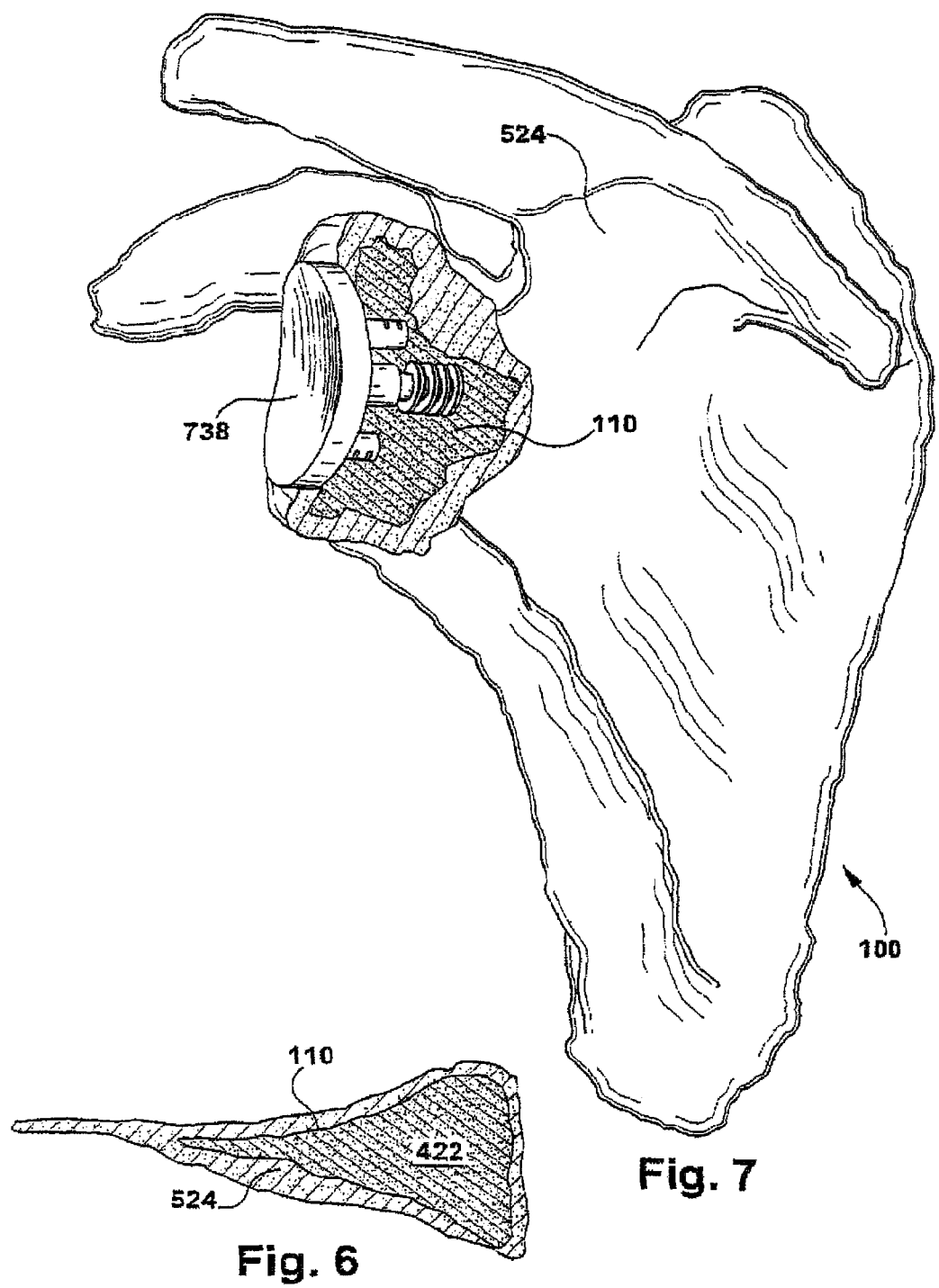

METHOD AND APPARATUS FOR PREPARING FOR A SURGICAL PROCEDURE

RELATED APPLICATIONS

This application is a continuation of U.S. patent application Ser. No. 13/197,265, filed 3 Aug. 2011, which is a continuation of U.S. patent application Ser. No. 12/043,634, filed 6 Mar. 2008 (now U.S. Pat. No. 8,014,984), which claims priority from U.S. Provisional Patent Application Ser. No. 60/905,211, filed 6 Mar. 2007, the subject matter of all of which is incorporated herein by reference in their entireties.

TECHNICAL FIELD

The present invention relates to a method and apparatus for preparing for a surgical procedure and, more particularly, to three-dimensional modeling of pathologic anatomy and comparison of the pathologic anatomy to normal anatomy.

BACKGROUND OF THE INVENTION

The scapula, commonly known as the "shoulder blade", is a flat, triangular bone that lies over the back of the upper ribs. A left scapula 100 is depicted in anterior, posterior, and left side views in FIGS. 1A, 1B, and 1C, respectively. The posterior surface of the scapula 100 can be readily felt through a patient's skin. The scapula 100 serves as an attachment point for some of the muscles and tendons of the arm, neck, chest, and back, and aids in the movements of the arm and shoulder. The scapula 100 is also well padded with muscle, so that great force is required to fracture it. The rear surface of each scapula 100 is divided into unequal portions by a spine 102. This spine 102 leads to a head 104, which bears two processes—the acromion process 106 that forms the tip of the shoulder and a coracoid process 108 that curves forward and down below the clavicle (collarbone, not shown). The acromion process 106 joins the clavicle and provides attachments for muscles of the arm and chest muscles. The acromion process 106 is a bony prominence at the top of the scapula 100. On the head 104 of the scapula 100, between the acromion and coracoid processes 106 and 108, is a depression or cavity called the glenoid vault 110, shown partially in dashed line in the Figures. The glenoid vault 110 joins with the head of the upper arm bone (humerus, not shown) in a ball-and-socket manner to enable articulation of the shoulder joint thereby formed.

For treatment of various problems with the shoulder, hip, or other body joint or bone (such as degenerative arthritis and/or traumatic injury), one method of providing relief to a patient is to replace the articulating surfaces with an artificial or prosthetic joint. In the case of a shoulder, the humerus and glenoid vault 110 articulating surfaces are replaced. In the case of a hip, the femur and acetabulum articulating surfaces can be replaced. Both of these examples are of ball-and-socket type joints. Hinge-type joints, such as the knee or elbow, and static/fixed skeletal components, such as the long bones of the arm or leg, could also be subject to replacement and/or repair by the implantation of artificial or prosthetic components, as could interfaces such as those between spinal vertebrae and intervertebral discs. For clarity of description, the subject application will be hereafter described as the rehabilitation and/or replacement of a patient's shoulder joint.

In such surgical procedures, pain relief, increased motion, and anatomic reconstruction of the joint are goals of the orthopedic surgeon. With multiple variations in human anatomy, prosthetic systems must be carefully designed and chosen to both accurately replicate the joints that they replace and maintain the natural symmetry of the joints on the left and right sides of the patient's body.

A shoulder replacement procedure may involve a partial shoulder replacement (not shown) or the total shoulder replacement shown in FIG. 2. In a total shoulder replacement procedure, a humeral component 212 having a head portion is utilized to replace the natural head portion of the upper arm bone, or humerus 214. The humeral component 212 typically has an elongated stem which is utilized to secure the humeral component to the patient's humerus 214, as depicted. In such a total shoulder replacement procedure, the natural bearing surface of the glenoid vault 110 is resurfaced, lined, or otherwise supplemented with a cup-shaped glenoid component 216 that provides a bearing surface for the head portion of the humeral component 212.

Standard prosthetic glenoid components 216 are available in a number of different sizes and configurations. However, most are designed for use in an anatomically normal scapula. When the scapula has abnormal pathology due to disease or trauma, the standard glenoid component 216 may be difficult to implant and/or may not enable desired shoulder function, once implanted. The surgeon may thus need to substantially modify the patient's glenoid vault 110 during surgery in an attempt to make the standard glenoid component 216 fit into the glenoid vault. Presurgery planning tools are available to help the surgeon anticipate the changes which will be needed to reform the patient's pathological anatomy. However, the surgeon cannot always readily determine whether even a remodeled glenoid vault 110 will fit as desired with a standard prosthesis because the surgeon does not know how a "normal" glenoid vault 110 (for which the standard prosthesis is designed) should be shaped for that patient.

It is known to use computer aided design ("CAD") software to design custom prostheses based upon imported data obtained from a computerized tomography ("CT") scan of a patient's body. For example, mirror-imaged CT data of a patient's contralateral "normal" joint could be used, if the contralateral joint does not also display a pathological anatomy. However, using a unique prosthesis design for each patient can result in future biomechanical problems and takes away the familiarity that the surgeon will likely have with standardized prosthesis designs. Thus, prosthesis designs that are entirely customized are considered sub-optimal solutions.

An example of a customized prosthesis and method of designing and making such using CT data is disclosed in U.S. Pat. No. 6,944,518 (hereafter referenced as "the '518 patent"). The '518 patent discloses a method of making a prosthesis for a joint socket in which CT data from a patient's joint is used to design the prosthesis. The CT data is downloaded into CAD software in order to design at least an attachment part, and possibly a functional part, of the prosthesis. The attachment part can be used to attach or otherwise associate the functional part to the patient's bone. The functional part can have standardized dimensions.

The attachment part of the '518 patent must be custom-made, which adds time and expense to the surgical preparation process. Moreover, biomechanical interaction between the functional prosthesis and the patient's joint will be altered in possibly unpredictable ways by the interposed attachment part. Finally, use of the attachment part prevents the patient's pathological anatomy from being corrected, and may even result in deterioration of the patient's native bone, which could cause further problems with the prosthetic joint and/or could complicate revision surgery.

SUMMARY OF THE INVENTION

In an embodiment of the present invention, a method of preparing for a surgical procedure is described. A three-dimensional bone model of a subject bone of a patient is created. At least a portion of the bone model is compared to at least one three-dimensional reference anatomic model. At least one structural difference between the bone model and the at least one reference anatomic model is identified. At least one desired subject bone structural change is specified to produce a modified bone model responsive to the step of identifying at least one structural difference between the bone model and the at least one reference anatomic model.

In an embodiment of the present invention, a method of performing a shoulder arthroplasty is described. A three-dimensional bone model of at least a portion of a scapula of a patient is created. At least a portion of the bone model is compared to at least one three-dimensional reference anatomic model. At least one structural difference between the bone model and the at least one reference anatomic model is identified. At least one desired subject bone structural change is specified to produce a modified bone model responsive to the step of identifying at least one structural difference between the bone model and the at least one reference anatomic model. At least one of the bone model and the modified bone model is associated with a three-dimensional prosthetic model of a prosthetic shoulder joint component. The scapula of the patient is adapted responsive to the step of specifying at least one desired subject bone structural change to produce a modified bone model. The scapula is mated with the prosthetic shoulder joint component.

In an embodiment of the present invention, a joint surgery preparation tool is described. Means for creating a three-dimensional joint model of a subject joint of a patient are provided. Means for comparing at least a portion of the joint model to at least one three-dimensional reference anatomic model are provided. Means for identifying at least one structural difference between the joint model and the at least one reference anatomic model are provided. Means for specifying at least one desired subject joint structural change to produce a modified joint model responsive to the means for identifying at least one structural difference between the joint model and the at least one reference anatomic model are provided.

BRIEF DESCRIPTION OF THE DRAWINGS

For a better understanding of the invention, reference may be made to the accompanying drawings, in which:

FIG. 6 is a side view similar to FIG. 5;

FIG. 7 is a partial sectional posterior view of a prosthetic shoulder joint component in a scapula.

DESCRIPTION OF EMBODIMENTS

In accordance with the present invention, a method and apparatus for preparing for a surgical procedure are provided. The surgical procedure will be described below as involving the implantation of a prosthetic shoulder joint component into a scapula. However, the method and apparatus of the present invention may each be used to prepare for any surgical procedure upon any body component of a patient including, but not limited to, total or partial replacement or repair of ball-and-socket joints, hinge joints, and fixed (i.e., non-joint) skeletal components. In addition, the below description presumes that the procedures described are largely being accomplished in a virtual manner, using a computer. However, it is also contemplated that the below procedures could be carried out using any desired combination of two- or three-dimensional physically manipulated (i.e., non-virtual) replicas of the actual components being referenced, or by using the components themselves.

Figure 1A:
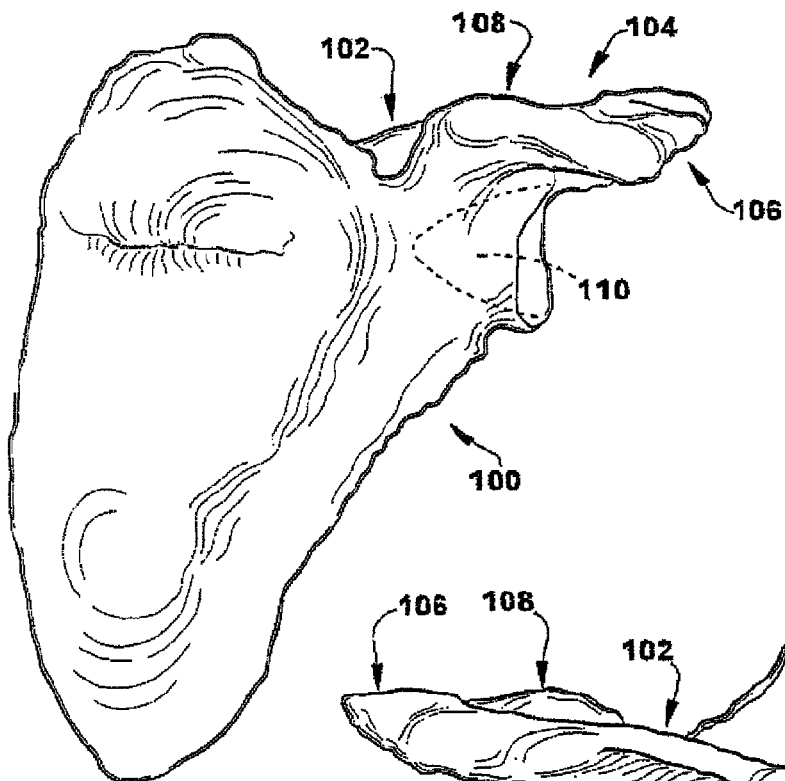
FIG. 1A is an anterior view of a left scapula.
Figure 1B:
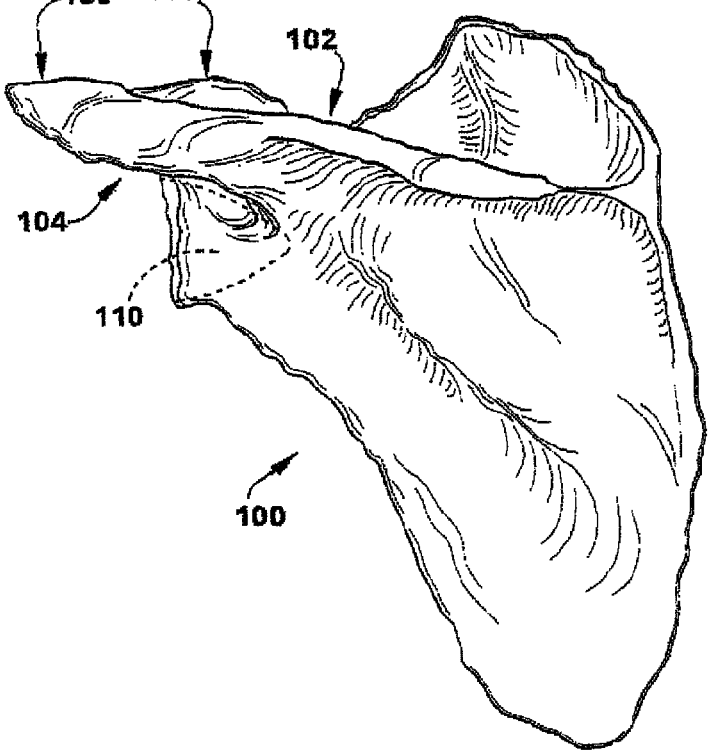
FIG. 1B is a posterior view of the scapula of FIG. 1A.
Figure 1C:
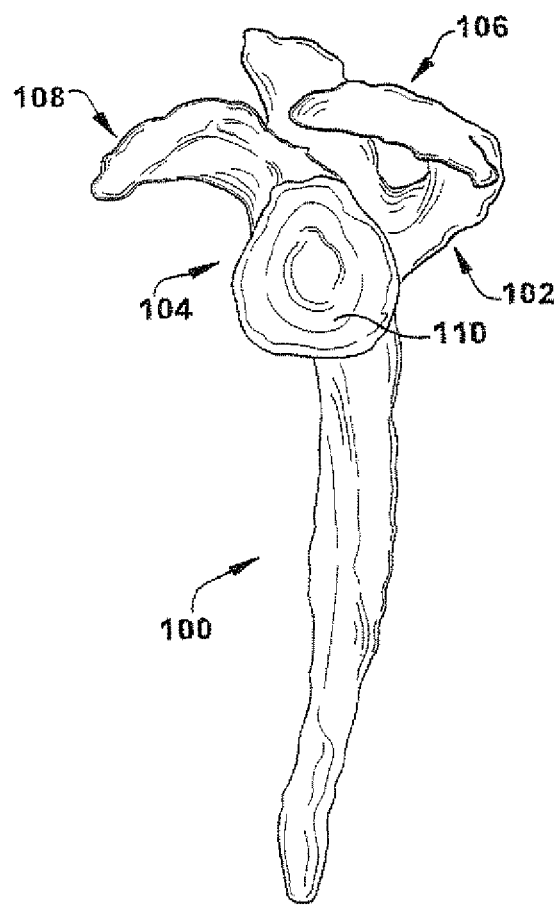
FIG. 1C is a side view of the scapula of FIG. 1A.
Figure 2:
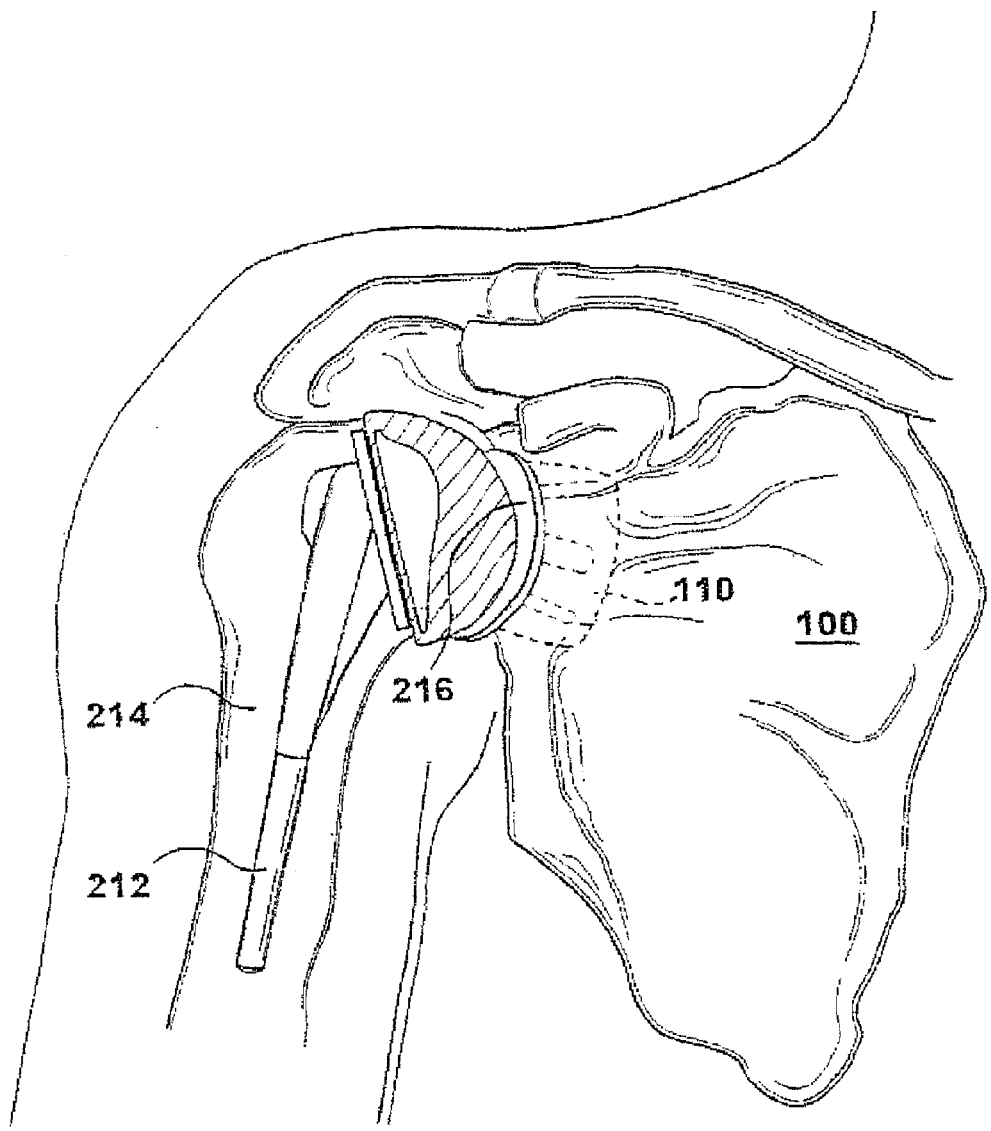
FIG. 2 is a partial sectional anterior view of a prosthetic shoulder joint in a patient.
Figure 3:
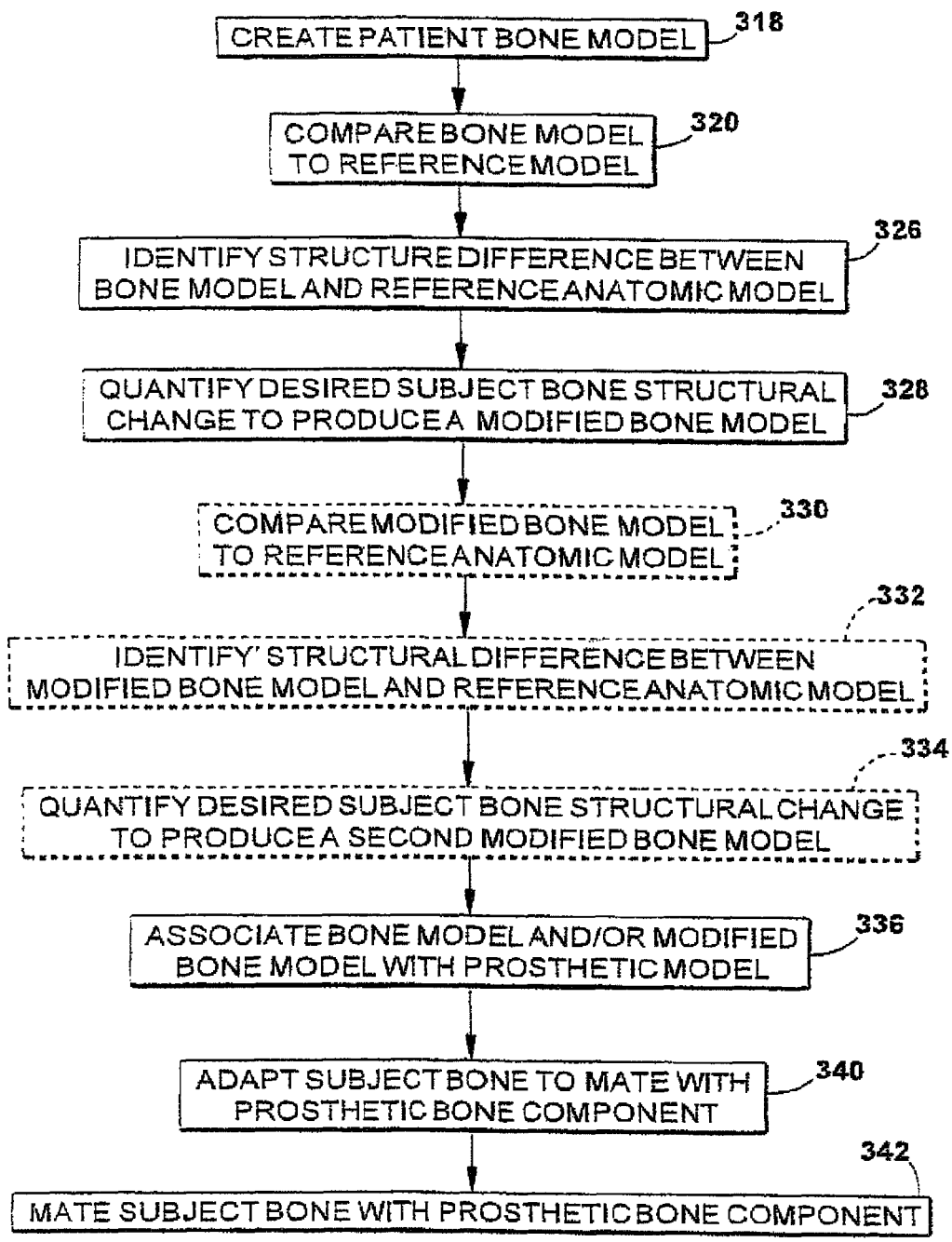
FIG. 3 is a flowchart of an embodiment of the present invention.

It is desirable for a health care professional (described hereafter as a surgeon) to be able to prepare for a surgery by reviewing the patient's existing bone structure and determining in advance the best methods and prosthetics to use in that surgery. The flowchart of FIG. 3 depicts a method by which a surgeon may prepare for, and optionally carry out, a described shoulder joint replacement surgery or shoulder arthroplasty. However, the steps shown in FIG. 3 may be used to prepare for, and carry out, any suitable surgical procedure, as previously mentioned.

Moreover, for purposes of simplicity of explanation, the methodology of FIG. 3 is shown and described as being executed serially. It is to be understood and appreciated that the present invention is not limited by the illustrated order, as some aspects could, in accordance with the present invention, occur concurrently with other aspects and/or in different orders from those shown and described herein. Additionally, not all illustrated features may be required to implement a methodology in accordance with an aspect of the present invention.

In block 318, a three-dimensional bone model of at least a portion of a subject bone (here, a scapula) of the patient is created. The term "model" is used herein to indicate a replica or copy of a physical item, at any relative scale and represented in any medium, physical or virtual. The bone model may be a total or partial joint model of a subject joint of the patient, and may be created in any suitable manner. For example, and as presumed in the below description, the bone model may be based upon computer tomography ("CT") data imported into a computer aided drafting ("CAD") system. Additionally or alternatively, the bone model may be based upon digital or analog radiography, magnetic resonance imaging, or any other suitable imaging means. The bone model, and any other models created using the described method, are optionally displayed for the surgeon to review and manipulate, such as through the use of a computer or other graphical workstation interface.

Once the bone model has been created, the patient's pathologic anatomy is captured and can be studied through observation and manipulation of the bone model. At block 320, at least a portion of the bone model is compared to at least one three-dimensional reference anatomic model. The reference anatomic model, which may be either previously defined or generated in response to the surgery being planned, should represent a "normal" example of the subject bone anatomy, and can be generated in a number of different ways.

For example, the reference anatomic model could be based upon another structure in the patient's body, such as a corresponding contralateral bone or a soft-tissue or bony structure which normally would interact with the subject bone. Alternatively, the reference anatomic model could be modeled upon a corresponding subject bone from another body, or an average structure of a plurality of corresponding subject bones from other bodies. The reference anatomic model could be a negative space reference anatomic model; i.e., the reference anatomic model could represent the space of a void in an anatomically normal corresponding subject bone, rather than representing a bony structure directly.

Figure 4:
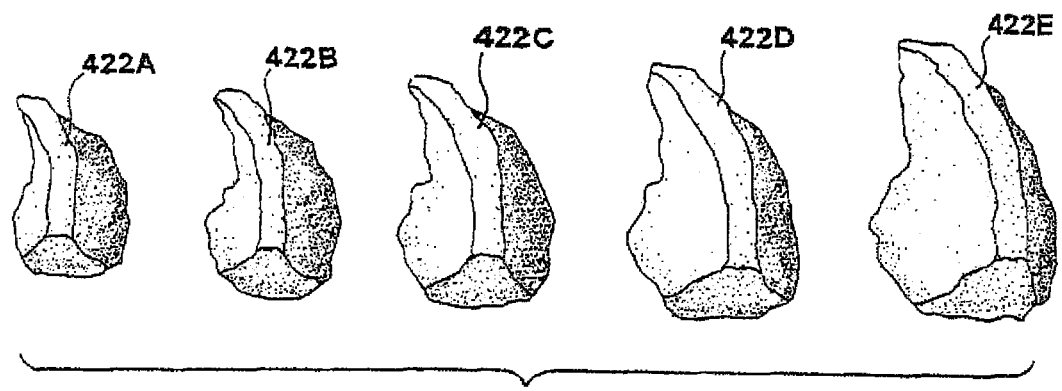
FIG. 4 is a top view of an array of glenoid vault implants according to an embodiment of the present invention.

As an example, FIG. 4 depicts a group of negative space reference anatomic models 422A, 422B, 422C, 422D, and 422E, which are glenoid vault implants. The glenoid vault implants 422A, 422B, 422C, 422D, and 422E are based upon an average shape of the glenoid vault 110 of a plurality of sample scapulae 100. More specifically, over sixty cadaver scapulae 100 were modeled, and the shapes of the glenoid vaults 110 of these scapulae were merged and specified to define an average glenoid vault 110 shape, represented in FIG. 4 by the middle-sized glenoid vault implant 422C. This average glenoid vault 110 shape was then scaled both up and down by ten and twenty percent to produce the range of five sizes of predetermined glenoid vault implants 422A, 422B, 422C, 422D, and 422E.

The glenoid vault implants 422A, 422B, 422C, 422D, and 422E, based upon the defined average glenoid vault 110 shape, were then compared to the actual glenoid vault 110 shapes of an additional eleven non-pathologic comparison scapulae 100 of various sizes. The size of each scapula 100 determined the specific glenoid vault implant 422A, 422B, 422C, 422D, and 422E to which that scapula's glenoid vault 110 would be compared. It was found that appropriately sized glenoid vault implants 422A, 422B, 422C, 422D, and 422E very closely correlated with the actual shape of a normal glenoid vault 110 of the comparison scapulae 100. Therefore, the glenoid vault implants 422A, 422B, 422C, 422D, and 422E can be considered to present accurate negative space reference anatomic models of anatomically normal glenoid vaults 110.

The reference anatomic model used for comparison to the bone model in block 320 may be a chosen one of a plurality of predefined three-dimensional reference anatomic models, in which case, at least a portion of the bone model is compared to the chosen reference anatomic model. For example, and as described above, a suitable glenoid vault implant 422 for comparison may be chosen from among a plurality of glenoid vault implants 422A, 422B, 422C, 422D, and 422E, according to a size of the patient's scapula 100. A library of predefined glenoid vault implants 422A, 422B, 422C, 422D, and 422E, or of any other desired full or partial bone shape or bone void shape for any type of surgical planning, could be provided to facilitate comparison of pathologic anatomies to normal anatomies of the same bone structures.

The comparison of block 320 may be accomplished, particularly when the reference anatomic model is a chosen negative space reference anatomic model, by mating the reference anatomic model to the bone model. The term "mating" is used herein to signify a substantial joining or fitting together, but two "mating" structures need not be precise or complete negative/positive images of one another.

Figure 5:
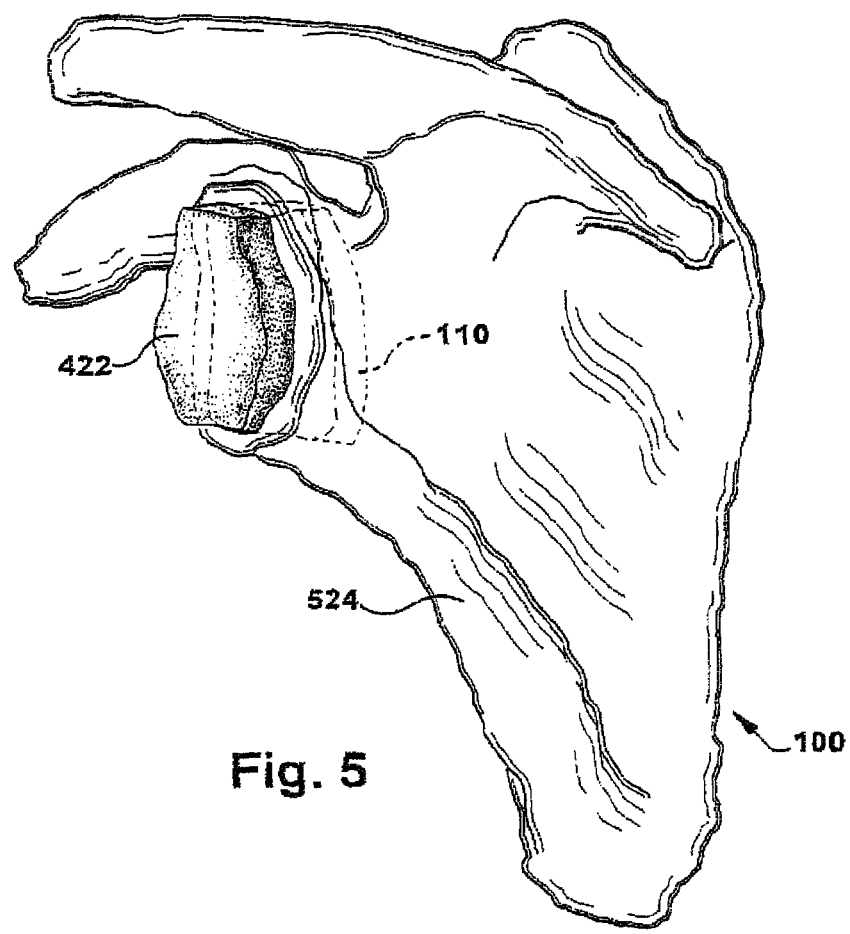
FIG. 5 is a partial perspective view of a glenoid vault implant of FIG. 4 in a scapula.

As shown in FIG. 5, when the bone model 524 represents a scapula 100, a glenoid vault implant 422 may be mated with the glenoid vault 110 area of the bone model 524. In the view of FIG. 5, the glenoid vault implant 422 may not have yet been fully mated with the bone model 524, as is suggested by the protrusion of the glenoid vault implant 422 from the glenoid vault 110. As another example, FIG. 6 is a side view of a glenoid vault implant 422 fully mated with a glenoid vault 110 of a bone model 524. As can be readily seen, the glenoid vault implant 422 closely follows the contours of the native glenoid vault 110. Accordingly, and at least in the view shown in FIG. 6, the bone model 524 seems to represent a scapula having normal, non-pathologic anatomy.

In contrast, the comparison of block 320 may result in a finding that the reference anatomic model does not mate smoothly with the bone model of the patient's anatomy, which is to be expected when the patient's bone exhibits pathologic anatomy to the extent that surgery on that bone is being planned. Returning to the flowchart of FIG. 3, the surgeon may next identify at least one structural difference between the bone model 524 and the reference anatomic model (here, the glenoid vault implant 422). Here, a virtual mating of the bone model 524 and the reference anatomic model may allow for the structural difference(s) to be automatically identified by a computer as being areas of substantial overlapping or gapping between the bone model and the reference anatomic model. The surgeon may also or instead identify the structural difference(s) between the bone model 524 and the reference anatomic model manually. Optionally, the surgeon may ignore or modify automatically identified structural difference(s).

Once one or more structural differences between the bone model 524 and the reference anatomic model have been identified, at least one desired subject bone structural change is specified, at block 328, to produce a modified bone model. The desired subject bone structural change(s) may be specified manually or automatically. The desired subject bone structural changes may each be specified in direct response to an identified structural difference. However, the desired subject bone structural changes may, instead, be specified independently from the identified structural difference(s) in response to the mere detection that at least one structural difference is present.

The modified bone model is produced in response to the identification of the structural difference(s) between the bone model 524 and the reference anatomic model and represents the desired subject bone structural changes which are predicted to bring the patient's pathologic bone structure closer to the normal anatomic bone structure represented by the reference anatomic model. These subject bone structural changes may include material removal, such as reaming, material addition, such as grafting, or any other structural changes made by any desired method. The surgeon may rely on their training and experience to adjust the specified subject bone structural change(s) as desired for a particular patient application of the present invention, until a suitable modified bone model has been produced.

Optionally, as shown by the dashed-line block 330 in FIG. 3, the modified bone model produced in the block 328 may be compared to at least one reference anatomic model. This check step may be performed to ensure that the modified bone model represents an accurate reconstruction of the patient's bone into a normal anatomical condition. At least one structural difference between the modified bone model and the reference anatomic model may be identified by the comparison in an optional block 332.

It is possible that there will be no remaining structural differences between the modified bone model and the reference anatomic model, so the identification step of the block 332 will then be complete. However, when at least one structural difference is found, at least one desired subject bone structural change may be specified, in the optional block 334 to produce a second modified bone model responsive to the identification of the structural difference(s) between the modified bone model and the reference anatomic model.

The steps of blocks 330, 332, and 334 could be repeated as many times as desired to refine successive iterations of the modified bone model. For ease of description, though, the term "modified bone model" will be used hereafter to reference without distinction either the initially created modified bone model, the second modified bone model, or any subsequent modified bone model. The modified bone model may be considered to represent the patient's pathologic bone after physical remodeling, and approximates an anatomically normal bone. However, the modified bone model need not be identical to a normal bone; one of ordinary skill in the art can readily choose and alter desired subject bone structural changes to create a modified bone model having an acceptable degree of remaining pathological features based upon the patient's needs and the physical constraints of the surgical procedures.

In the block 336, and as illustrated in FIG. 7, at least one of the bone model 524 and the modified bone model is associated with a three-dimensional prosthetic model of a prosthetic bone component 738. In FIG. 7, the bone model 524 is of a scapula 100 in which the glenoid vault 110 is of an anatomically normal configuration, and the prosthetic bone component 738 is a prosthetic shoulder joint glenoid vault component. There is no distinction in the method shown in FIG. 3, at block 336 and beyond, of whether an anatomically normal feature of a bone model 524 has resulted from the patient's own normal pathology or from at least one desired subject bone structural change to create a modified bone model.

The prosthetic model 738 may depict a custom prosthetic bone component created, manually or automatically, responsive to the step of block 326, in which at least one structural difference between the bone model and the reference anatomic model is identified. A custom prosthetic bone component may also or instead be created with reference to the modified bone model.

If a standard, or noncustom, prosthetic bone component is instead desired for use, one of a plurality or library of predefined prosthetic bone components could be chosen, manually or automatically. Each of the predefined prosthetic bone components may have an associated prosthetic model 738 for use in surgical planning. The choice of a predefined prosthetic bone component could be made with reference to the modified bone model and/or in response to the step of the block 326, in which at least one structural difference between the bone model and the reference anatomic model is identified.

As shown in FIG. 7, the prosthetic bone component 738 may be virtually mated with the bone model 524 or modified bone model. In the association step of the block 336, the prosthetic model 738 may be manipulated with respect to the bone model 524 or modified bone model, either manually or automatically, to achieve a desired relative positioning between the two structures. This manipulation may result in the identification of at least one desired subject bone structural change needed to mate the bone model 524 or modified bone model with the prosthetic model 738. The desired subject bone structural change identified through manipulation of the prosthetic model 738 may result in the creation of a modified bone model which either more or less closely approximates the reference anatomic model. However, at this stage of the surgical planning, it may be more important for the modified bone model to mate with the prosthetic model 738 as desired than for the modified bone model to mimic the reference anatomic model.

Once all of the desired subject bone structural changes are identified, using the surgeon's own determination and/or comparison of various combinations of the bone model 524, modified bone model, prosthetic model 738, and reference anatomic model, the surgeon may actually perform the desired subject bone structural changes upon the patient's bone. In other words, and as shown in the flowchart of FIG. 3 as block 340, the subject bone is adapted to mate with the prosthetic bone component. The surgeon might first perform this adaptation virtually, perhaps in a "practice mode" of a computer simulator, before actual surgery upon the patient.

Regardless of whether the surgeon is able to practice the adaptation in advance, the actual surgery may be performed on the patient and the subject bone may be actually modified to mate with the prosthetic bone component, using bone grafts, reamers, or any other suitable tools/techniques. The net effect of the desired subject bone structural changes is optionally, but not necessarily, to remodel the patient's pathologic anatomy to more closely resemble a previously established normal anatomy for that area of the body. Physical and/or surgical constraints, or choices by the surgeon, may prevent the patient's anatomy from being remodeled into a more normal structure. In any case, once the patient's bone is remodeled in a desired manner, conventional or unconventional surgical techniques may be used, as shown in block 342, to mate the patient's bone with the prosthetic bone component in an implantation procedure.

The surgery to adapt the subject bone may be performed in advance of the surgery to implant the prosthetic bone component, particularly if the surgeon desires the subject bone to heal, for example, to more firmly bond with a bone graft, before the prosthetic bone component is implanted into the patient's body.

The preoperative surgical planning process described above may be performed using a computer simulation visual interface. When available, a haptic interface may also be provided and linked to the visual interface so that a surgeon could practice the surgery, or certain steps thereof. The benefit of force feedback technology could therefore be used to help prepare the surgeon for both visual and tactile aspects of the surgery.

A computer used in the preoperative surgical planning process could also be used to assist the actual surgery upon the patient. For example, the computer could control a robotic surgical assistance structure to perform some or all of the steps needed to carry out the surgery in a desired manner.

Optionally, multiple bones or other anatomical structures could be modeled, possibly with prosthetic components associated with one or more of the anatomical structures. The modeled structures could be moved relative to one another to simulate a movement of the patient. In this manner, biomechanical testing could be carried out and used to refine the planned surgical procedures to achieve a desired result for that patient.

It is contemplated that, while the method and apparatus described above may be used for preoperative surgical planning to facilitate the implantation of a prosthetic component into at least one bone, joint, and/or soft tissue of a patient. However, one of ordinary skill in the art could readily perform selected portions of the surgical planning procedures to instead plan a surgery to modify a patient's anatomy from a pathological to a normal condition, with no prosthetic implantations performed. For example, a non-articular surface or portion of the bone (i.e., a fixed skeletal component) could be broken and re-set to normalize a pathologic anatomy.

Figure 8:
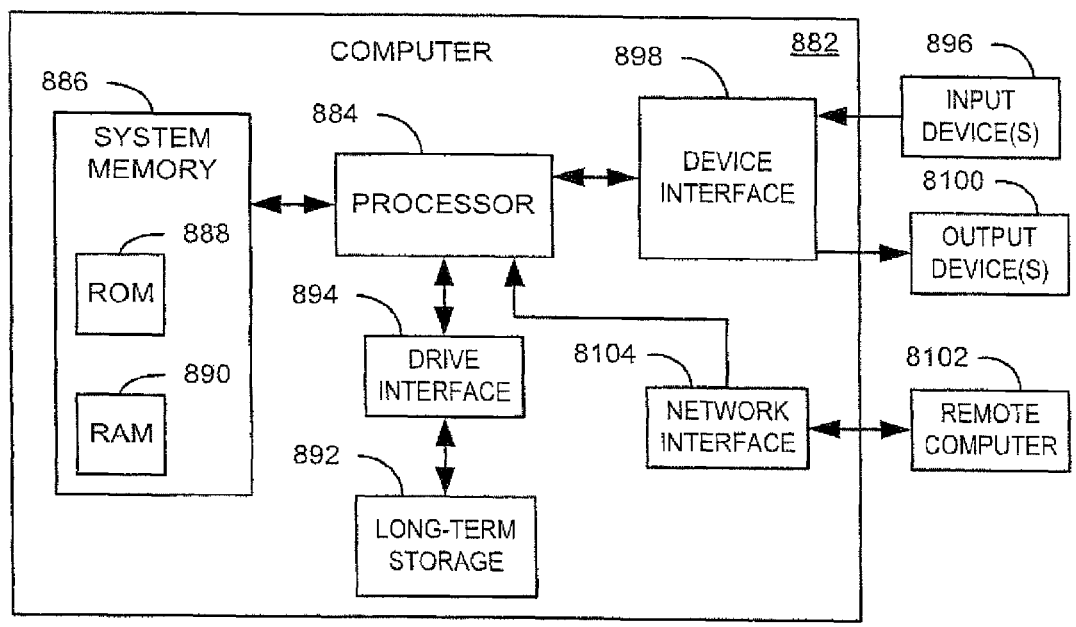
FIG. 8 is a schematic view of a computer system that can be employed to implement systems and methods described herein, such as based on computer executable instructions running on the computer system.

FIG. 8 illustrates a computer system 882 that can be employed to implement systems and methods described herein, such as based on computer executable instructions running on the computer system. The user may be permitted to preoperatively simulate the planned surgical procedure using the computer system 882 as desired. The computer system 882 can be implemented on one or more general purpose networked computer systems, embedded computer systems, routers, switches, server devices, client devices, various intermediate devices/nodes and/or stand alone computer systems. Additionally, the computer system 882 can be implemented as part of the computer-aided engineering (CAE) tool running computer executable instructions to perform a method as described herein.

The computer system 882 includes a processor 884 and a system memory 886. Dual microprocessors and other multiprocessor architectures can also be utilized as the processor 884. The processor 884 and system memory 886 can be coupled by any of several types of bus structures, including a memory bus or memory controller, a peripheral bus, and a local bus using any of a variety of bus architectures. The system memory 886 includes read only memory (ROM) 888 and random access memory (RAM) 890, which can both be considered computer-readable storage media. A basic input/output system (BIOS) can reside in the ROM 888, generally containing the basic routines that help to transfer information between elements within the computer system 882, such as a reset or power-up.

The computer system 882 can include one or more types of long-term data storage 892 or other computer-readable storage media, including a hard disk drive, a magnetic disk drive, (e.g., to read from or write to a removable disk), and an optical disk drive, (e.g., for reading a CD-ROM or DVD disk or to read from or write to other optical media). The long-term data storage 892 can be connected to the processor 884 by a drive interface 894894. The long-term data storage 892 components provide nonvolatile storage of data, data structures, and computer-executable instructions for the computer system 882. A number of program modules may also be stored in one or more of the drives as well as in the RAM 890, including an operating system, one or more application programs, other program modules, and program data.

A user may enter commands and information into the computer system 882 through one or more input devices 896, such as a keyboard or a pointing device (e.g., a mouse). These and other input devices are often connected to the processor 884 through a device interface 898. For example, the input devices can be connected to the system bus by one or more a parallel port, a serial port or a universal serial bus (USB). One or more output device(s) 8100, such as a visual display device or printer, can also be connected to the processor 884 via the device interface 898.

The computer system 882 may operate in a networked environment using logical connections (e.g., a local area network (LAN) or wide area network (WAN) to one or more remote computers 8102. A given remote computer 8102 may be a workstation, a computer system, a router, a peer device or other common network node, and typically includes many or all of the elements described relative to the computer system 882. The computer system 882 can communicate with the remote computers 8102 via a network interface 8104, such as a wired or wireless network interface card or modem. In a networked environment, application programs and program data depicted relative to the computer system 882, or portions thereof, may be stored in memory associated with the remote computers 8102, which can also be considered a computer-readable storage medium.

While aspects of the present invention have been particularly shown and described with reference to the preferred embodiment above, it will be understood by those of ordinary skill in the art that various additional embodiments may be contemplated without departing from the spirit and scope of the present invention. For example, though described as useful for orthopedic/bone surgical procedures, soft-tissue surgical procedures could also benefit from the apparatus and method described herein. The above procedures are described as being performed on three-dimensional models; however, one or more two-dimensional depictions of the described objects may instead be used/compared, presuming that those two-dimensional depictions are sufficient to perform the described evaluation steps adequately. Any procedure described as being performed on one of the bone model, reference anatomic model, modified bone model, and prosthetic model could also or instead be performed upon another structure of that group. Multiple reference anatomic models could be compared to at least one of the bone model and the modified bone model, simultaneously or in sequence. The prosthetic bone components may include portions of both custom and standard/predefined structures. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A method of preparing for a surgical procedure, the method comprising the steps of:
   creating, using a computer, a three-dimensional bone model of a subject bone of a patient;
   comparing, using the computer, at least a portion of the bone model to at least one three-dimensional reference anatomic model, wherein the at least one reference anatomic model is a negative space reference anatomic model, and comparing at least a portion of the bone model to at least one three-dimensional reference anatomic model includes mating the at least one reference anatomic model to the bone model;
   identifying, using the computer, at least one structural difference between the bone model and the at least one reference anatomic model; and
   specifying, using the computer, at least one desired subject bone structural change to produce a modified bone model responsive to the step of identifying at least one structural difference between the bone model and the at least one reference anatomic model.

2. The method of claim 1, including the steps of:
   comparing at least a portion of the modified bone model to the at least one reference anatomic model;
   identifying at least one structural difference between the modified bone model and the at least one reference anatomic model; and
   specifying at least one desired subject bone structural change to produce a second modified bone model responsive to the step of identifying at least one structural difference between the modified bone model and the at least one reference anatomic model.

3. The method of claim 1, including the step of associating at least one of the bone model and the modified bone model with a three-dimensional prosthetic model of a prosthetic bone component.

4. The method of claim 3, wherein the step of associating at least one of the bone model and the modified bone model with a three-dimensional prosthetic model of a prosthetic bone component includes the step of identifying at least one desired subject bone structural change needed to mate the at least one of the bone model and the modified bone model with the prosthetic model.

5. The method of claim 4, including the step of adapting the subject bone of the patient to mate with the prosthetic bone component responsive to the step of identifying at least one desired subject bone structural change needed to mate the at least one of the bone model and the modified bone model with the prosthetic model.

6. The method of claim 1, including the step of creating a custom prosthetic bone component responsive to the step of identifying at least one structural difference between the bone model and the at least one reference anatomic model.

7. The method of claim 1, including the step of choosing one of a plurality of predefined prosthetic bone components responsive to the step of identifying at least one structural difference between the bone model and the at least one reference anatomic model.

8. The method of claim 1, wherein the step of comparing at least a portion of the bone model to at least one three-dimensional reference anatomic model includes the steps of:
choosing one of a plurality of predefined three-dimensional reference anatomic models; and
comparing at least a portion of the bone model to the chosen reference anatomic model.

9. The method of claim 1, wherein the subject bone is at least a portion of a joint.

10. The method of claim 1, wherein the subject bone is at least a portion of a fixed skeletal component.

11. A method of performing a shoulder arthroplasty, the method comprising the steps of:
creating, using a computer, a three-dimensional bone model of at least a portion of a scapula of a patient;
comparing, using the computer, at least a portion of the bone model to at least one three-dimensional reference anatomic model, wherein comparing at least a portion of the bone model to at least one three-dimensional reference anatomic model includes mating a predefined glenoid vault negative space model with a glenoid vault portion of the bone model;
identifying, using the computer, at least one structural difference between the bone model and the at least one reference anatomic model;
specifying, using the computer, at least one desired subject bone structural change to produce a modified bone model responsive to the step of identifying at least one structural difference between the bone model and the at least one reference anatomic model;
associating at least one of the bone model and the modified bone model with a three-dimensional prosthetic model of a prosthetic shoulder joint component;
adapting the scapula of the patient responsive to the step of specifying at least one desired subject bone structural change to produce a modified bone model; and
mating the scapula with the prosthetic shoulder joint component.

12. The method of claim 11, including the steps of:
comparing at least a portion of the modified bone model to the at least one reference anatomic model;
identifying at least one structural difference between the modified bone model and the at least one reference anatomic model; and
specifying at least one desired subject bone structural change to produce a second modified bone model responsive to the step of identifying at least one structural difference between the modified bone model and the at least one reference anatomic model.

13. The method of claim 11, wherein the step of associating at least one of the bone model and the modified bone model with a three-dimensional prosthetic model of a prosthetic shoulder joint component includes the step of identifying at least one desired subject bone structural change needed to mate the at least one of the bone model and the modified bone model with the prosthetic model.

14. The method of claim 11, including the step of creating a custom prosthetic shoulder joint component responsive to the step of identifying at least one structural difference between the bone model and the at least one reference anatomic model.

15. The method of claim 11, including the step of choosing one of a plurality of predefined prosthetic shoulder joint components responsive to the step of identifying at least one structural difference between the bone model and the at least one reference anatomic model.

16. The method of claim 11, wherein the step of comparing at least a portion of the bone model to at least one three-dimensional reference anatomic model includes the steps of:
choosing one of a plurality of predefined three-dimensional reference anatomic models; and
comparing at least a portion of the bone model to the chosen reference anatomic model.

* * * * *